United States Patent [19]
Matsuo et al.

[11] Patent Number: 5,973,134
[45] Date of Patent: *Oct. 26, 1999

[54] RAT CNP COMPLEMENTARY DNA AND PRECURSOR PROTEIN

[75] Inventors: Hisayuki Matsuo, Osaka; Masayasu Kojima; Kenji Kangawa, both of Miyazaki-ken; Naoto Minamito, Osaka, all of Japan

[73] Assignees: Suntory Limited; Hasayuki Matsuo, both of Osaka, Japan

[ * ] Notice: This patent is subject to a terminal disclaimer.

[21] Appl. No.: 07/757,606

[22] Filed: Sep. 11, 1991

[30] Foreign Application Priority Data

Sep. 11, 1990 [JP] Japan .................................. 2-241074

[51] Int. Cl.$^6$ ............................. C07H 17/00; C07K 14/00
[52] U.S. Cl. ....................................... 536/23.53; 530/350
[58] Field of Search .................................. 536/27, 23.53; 530/350, 325

[56] References Cited

FOREIGN PATENT DOCUMENTS 0466175  1/1992  European Pat. Off. .

OTHER PUBLICATIONS

Kojima et al. 1990 FEBS 276:209–213.
Minamino et al. 1990 Biochem Biophys. Res. Commun. 170:973.
Minamino et al; N–Terminally Extended Form of C–Type Nartriuretic Peptide (CNP–53) Identified in Porcine Brain; Biochemical and Biophysical Research Communications; vol. 170, No. 2, Jul. 31, 1990, pp. 973–979.
Kojima et al, Cloning and sequence analysis of cDNA encoding a precursor for a rat brain nattriuretic peptide; Biochemical and Biophysical Research Communications; vol. 159, No. 3, Mar. 31, 1989, pp. 1420–1426.
Kojima et al, Cloning and sequence analysis of a cDNA encoding a precursor for rat C–type natriuretic peptide (CNP), Febs Letters, vol. 276, No. 1/2, Dec. 1990, pp. 209–213.
Kita et al. 1989. Life Science 44:1541–1545.
Steinhelper et al 1990 Hypertension 16(3):301–307, Abstract.
Seilhamer et al. 1989 Biochem Biophys Res Commun 165:650–658.
Lazure et al 1988 FEBS Lett. 238:300–306.
Vlasuk et al. 1986 Biochem Biophys Res Commun 136:396–403.

*Primary Examiner*—Karen Cochrane Carlson
*Attorney, Agent, or Firm*—Pillsbury Madison & Sutro LLP

[57] ABSTRACT

A cDNA coding for a rat derived CNP (rCNP: C-type natriuretic pepteide), and a rat derived CNP precursor protein and derivatives thereof are disclosed.

The rat derived CNP precursor is represented by the following amino acid sequence.

Met His Leu Ser Gln Leu Ile Ala Cys Ala Leu Leu Leu Ala Leu Leu Ser Leu Arg Pro Ser Glu Ala Lys Pro Gly Thr Pro Pro Lys Val Pro Arg Thr Pro Pro Gly Glu Glu Leu Ala Glu Pro Gln Ala Ala Gly Gly Asn Gln Lys Lys Gly Asp Lys Thr Pro Gly Gly Gly Ala Asn Leu Lys Gly Asp Arg Ser Arg Leu Leu Arg Asp Leu Arg Val Asp Thr Lys Ser Arg Ala Ala Trp Ala Arg Leu Leu His Glu His Pro Asn Ala Arg Lys Tyr Lys Gly Gly Asn Lys Lys Gly Leu Ser Lys Gly Cys Phe Gly Leu Lys Leu Asp Arg Ile Gly Ser Met Ser Gly Leu Gly Cys

The rCNP precursor and its derivatives are novel and have natriuretic and hypotensive activities.

4 Claims, 4 Drawing Sheets

```
SmaI
  1 CCCGGGGGCGGTGGGCTCGCCTTCTGCACGAGCACCCCAACGCGCGCAAATACA   54
    ArgAlaAlaTrpAlaArgLeuLeuHisGluHisProAsnAlaArgLysTyrL

55 AAGGGCGCAACAAGAAGGGCTTGTCCAAAGGCTGCTTTGGCCTCAAGCTGGACC  108
    ysGlyGlyAsnLysLysGlyLeuSerLysGlyCysPheGlyLeuLysLeuAspA
                                                      MvaI

109 GGATCGGCTCCATGAGCGGGTCTGGGATGTTAGTGCAGCGACCCCTGGGGGGT  162
    rgIleGlySerMetSerGlyLeuGlyCys***

163 GAGTAACACCATCAGACGCTCCCCGCTCGCCCAGCTCTGCAACGCGGAGAACC  216

217 AAGCTCTATCACTGCCCTTCGCCAGACTGTTTGGTTTCCTCCCTGACCCTATGC  270

271 CCTGTGACCTTCCCCCAACCGATTTGAGCATGAGATCAAGTGAAATCCAGACAT  324

325 TTGCCTGCTACCTTACATATCCCATTTACAAATTAATGAAATGAACTGAACAT  378

379 AGGCCAGGTCAGAGACTGGGCTCAGCCTTAGAGTACCCCATCTGGCTTCCTCTA  432

433 GA
    XbaI
```

| Fig. 2 |
|---|
| Fig. 2a |
| Fig. 2b |

Fig. 2a

```
-116  CC GCA CAG CAG TAG GAC CCG  -97
-96   TGC TCG CTT GGC AAT CCT GCT CTG CAA CCG CTT GTC CTC GGT CCC ATC GGC ACC  -49
-48   GGC CGT CCC GGC TGC AGA CTG TCT GCA CCC CTC CTG CTG CTC CTA CTC            -1
                                                          10
1     ATG CAC CTC TCC CAG CTG ATC CTC ATT GCC TGT GCC CTG CTG CTC GCG CTA CTC   48
      Met His Leu Ser Gln Leu Ile Leu Ile Ala Cys Ala Leu Leu Leu Ala Leu Leu
                       20                                30
49    TCA CTC CGG CCC GAA TCC GGG GCC AAG CCC GGG ACA CCA CCG AAG GTC CCG        96
      Ser Leu Arg Pro Glu Ser Gly Ala Lys Pro Gly Thr Pro Pro Lys Val Pro
                                40
97    AGA ACC CCG CCA GGG GAG GAG CTG GCA CTG GAG CCC CAG GCA GCT GGT GGC       144
      Arg Thr Pro Pro Gly Glu Glu Leu Ala Leu Glu Pro Gln Ala Ala Gly Gly
                   50                                60
145   AAT CAG AAA AAG GGT GAC AAG ACT CCA ACT CCA GGC GGG GGA GCC AAT CTC       192
      Asn Gln Lys Lys Gly Asp Lys Thr Pro Thr Pro Gly Gly Gly Ala Asn Leu
                                70                                80
193   AAG GGA GAC CGA TCG CGA GAC CTG CTT CGG GAC CTG CGT GTG GAC ACC AAG       240
      Lys Gly Asp Arg Ser Arg Asp Leu Leu Arg Asp Leu Arg Val Asp Thr Lys
                   90
241   TCC CGG CGG GCG GCA TGG GCT CTT CGC CTG GAG CAC CCC AAC GCG CGC           288
      Ser Arg Ala Ala Trp Ala Leu Arg Leu Glu His Pro Asn Ala Arg
                        100                               110
289   AAA TAC AAA GGC AAC GGC GGG TTG TCC AAA GGC TGC TTT GGC                   336
      Lys Tyr Lys Gly Asn Gly Gly Leu Ser Lys Gly Cys Phe Gly
```

Fig. 2b

```
                                                        120                         126
337  CTC AAG CTG GAC CGG ATC GGC TCC ATG AGC GGT CTG GGA TGT TAG TGC  384
     Leu Lys Leu Asp Arg Ile Gly Ser Met Ser Gly Leu Gly Cys ***
385  AGC GAC CCC TGG CGG ATT GGG AAC TGC ACT GTG CAC TGA GGT CAT  432
433  CCT TGG TCA TCA GCC TCC AGC ATC TTT TCC TCC TGG AAA CAC CTC CAA CGC AAT GTG  480
481  GCT TTT ACA TTT CTT GTT TTA TTA TTT TGA AAA CAC CTC CAA CGC AAT GTG  480
```

```
                                                        120                         126
337  CTC AAG CTG GAC CGG ATC GGC TCC ATG AGC GGT CTG GGA TGT TAG TGC  384
     Leu Lys Leu Asp Arg Ile Gly Ser Met Ser Gly Leu Gly Cys ***
385  AGC GAC CCC TGG CGG ATT GGG AAC TGC ACT GTG CAC TGA GGT CAT       432
433  CCT TGG TCA TCA GCC TCC AGC ATC TTT TCC TCC TGG TAC CAA TAC ACA  480
481  GCT TTT ACA TTT CTT GTT TTA TTA TTT GGG AGG GGA TGA TTT TAT       528
529  ACA CCA GCT GTT TTT TTT TGA AAA TGA AAA ATA AAA AAT TAT ATA TTA  576
577  TGT TTG GGG TTT TAT ATA CAT GAG ACA CAC ACT CCC ACA CCG ACT TGA TGA  624
625  TAT ATA TAT ATA TAT AAA GTG ACT GAC AAA ACC AGC TAG CTG TAA AAA  672
673  CAA GGG ACG GTT TTT AAA ATT CAC ATC ATG CAT AAA TGT ATT TAT GTT GTA  720
721  CAT TGC TGT TTG TAA ATT TTG TTT ATA AAG AGA TAT TTA TAA AAA TTT TAT TTA  768
769  AAG CTA TTT ATA TTG TTT ATA AAG AGA TAT TTA TAA AAA TTT TAT TTA  816
817  TGT AAC TAA ATG AAA GAA GCC AAC CAT TGT AAT GTT TTT GTC CTA ACT  864
865  AGT TGA AAA AAA ATG TTA AAA AAA AAG CCA TTC CAT G(Poly A)         904
```

RAT CNP COMPLEMENTARY DNA AND PRECURSOR PROTEIN

BACKGROUND OF THE INVENTION

This invention relates to a cDNA coding for a rat CNP (rat C-type natriuretic peptide which is hereunder abbreviated as rCNP), as well as the rCNP precursor protein (prepro rCNP) that is encoded by said cDNA.

In recent years, various peptides collectively referred to as "natriuretic peptides" (NP) have been discovered from the atria and brains of various animals. Today those NPs can be classified into three types, A-type natriuretic peptide (ANP), B-type natriuretic peptide (BNP) and C-type natriuretic peptide (CNP), depending on similarities in the primary amino acid sequence and the structure of their precursors. Among the three types, ANP and BNP were first isolated and identified from the atrium and brain and hence are sometimes called "atrial natriuretic peptide" and "brain natriuretic peptide", respectively (Matsuo, H. and Nakazato, H., Endocrinol. Metab. Clin. North Am., 16, 43, 1987; Sudoh, T. et al., Nature, 332, 78, 1988). However, it is known today that ANP occurs not only in the atrium but also in the brain and that BNP occurs not only in the brain but also in the atrium. Further, both ANP and BNP exhibit significant natriuretic and hypotensive actions, so it has become clear that each of these peptides works not only as a hormone to be secreted from the atrium into blood but as a nerve transmitter in the brain, in either case helping regulate the homeostatic balance of body fluid volume and blood pressure in mammals.

The CNP has very recently been isolated and identified from porcine brain by Sudoh et al. as a third type of NP that is assignable to neither ANP nor BNP (Sudoh, T. et al., Biochem. Biophys. Res. Commun., 168, 863, 1990). The first discovered CNP consisted of 22 amino acid residues (this peptide is hereunder abbreviated as "pCNP-22"). Like ANP and BNP, CNP contained two cysteine residues which formed an intramolecular disulfide bond, producing a ring structure composed of 17 amino acid residues. Further, the primary amino acid sequence forming that ring structure in pCNP-22 was found to be highly homologous to that in ANP and BNP.

However, pCNP-22 differs from ANP and BNP in that the latter have several amino acid residues additionally attached to the C-terminus of the ring structure whereas no such "tail structure" is present in pCNP-22. In other words, the C-terminus of pCNP-22 is terminated with a cysteine residue. On the basis of these facts, it has been found that the structure of pCNP-22 is similar to but clearly distinguishable from those of ANP and BNP. In addition, pCNP-22 exhibited natriuretic and hypotensive actions and it was also found to display a higher activity than ANP and BNP in relaxant activity tests on chick rectal samples. From these observations, pCNP-22 was found to be an NP assignable to a new type, the peptides of which were named "CNPs".

Following pCNP-22, a second peptide assignable as CNP was isolated and identified from porcine brain by the present inventors. The peptide was found to consist of 53 amino acid residues with pCNP-22 present at the C-terminus (this peptide is hereunder abbreviated as pCNP-53). In other words, pCNP-53 was found to be a peptide that had 31 more amino acid residues attached to the N-terminus of pCNP-22. Interestingly enough, pCNP-53 has been found to occur in a greater amount than pCNP-22 in porcine brain (commonly assigned Japanese Patent Application No. 186582/1990).

Another very recent study succeeded in identifying the structure of the precursor of pCNP-22 and pCNP-53 by gene analysis and this helped unravel the mechanism behind the biosynthesis of those peptides (commonly assigned Japanese Patent Application No. 186583/1990). The present inventors isolated and identified a porcine chromosomal gene and cDNA coding for pCNP-22 and pCNP-53; by their analysis, the structure of the porcine CNP precursor protein (prepro pCNP) was unravelled; at the same time, it was found that each of pCNP-22 and pCNP-53 was first translated from mRNA as a prepro pCNP composed of 126 amino acid residues and that the signal peptide present in the N-terminal region of the precursor protein was then cleaved in the process of secretion to be converted to pro pCNP, which was further cleaved specifically with processing enzymes to be converted to pCNP-53 or pCNP-22 as appropriate. On the basis of these observations, it has been found that as in the case of ANP and BNP, both pCNP-22 and pCNP-53 are secretory peptides that are biosynthesized from a common precursor protein (prepro pCNP).

However, in sharp contrast with the peptides assignable to ANP and BNP which have been found by previous studies to work not only as hormones to be secreted from the atrium into blood but also as nerve transmitters in the brain, thereby regulating the homeostatic balance of body fluid volume and blood pressure, CNP remains unclear in many points as regards details of its distribution in vivo and physiological actions.

As for ANP and BNP, their structures have been established in rats and the physiological actions in rats of rat ANP and BNP have also been unravelled, with the evaluation of their pharmaceutical efficacy being conducted with care being taken to eliminate possible effects due to differences in animal species. However, as of today, the structure of CNP has not been identified in rats.

SUMMARY OF THE INVENTION

The present invention has been accomplished under these circumstances and has an object identifying the structures of CNPs in rats (rCNP), particularly those of rat CNPs that correspond to pCNP-22 and pCNP-53, as well as: the structure of their precursor protein which corresponds to prepro pCNP in porcine.

DETAILED DESCRIPTION OF THE INVENTION

Noting that the amino acid sequence of ANP and the base sequence of the gene encoding it are both retained with high homology across animal species, the present inventors thought that there would be a high likelihood for the same situation to occur in CNP. Based on this assumption, the present inventors projected a program in which the cDNA of rCNP was isolated using the DNA probe (pDC-53) which they used previously in isolating the chromosomal gene or cDNA of porcine CNP and the isolated cDNA was analyzed to identify the structure of the precursor protein of rCNPs.

In accordance with this program, the present inventors first screened a rat chromosomal gene library (λ-phage vector incorporating a chromosomal gene fragment) using pDC-53 as a DNA probe and obtained 5 clones that hybridized with pDC-53 under mild conditions. Analysis of one of those clones (λrCNP G3) showed that said clone harbored ca. 14 kbp of the rat chromosomal gene and that a BamHI DNA fragment of ca. 2.1 kbp of that 14 kbp hybridized with the pDC-53 DNA probe. When part of this BamHI DNA fragment of ca. 2.1 kbp was determined for its base sequence, it became apparent that the DNA of interest would code for the rCNP gene.

Figure 1A:
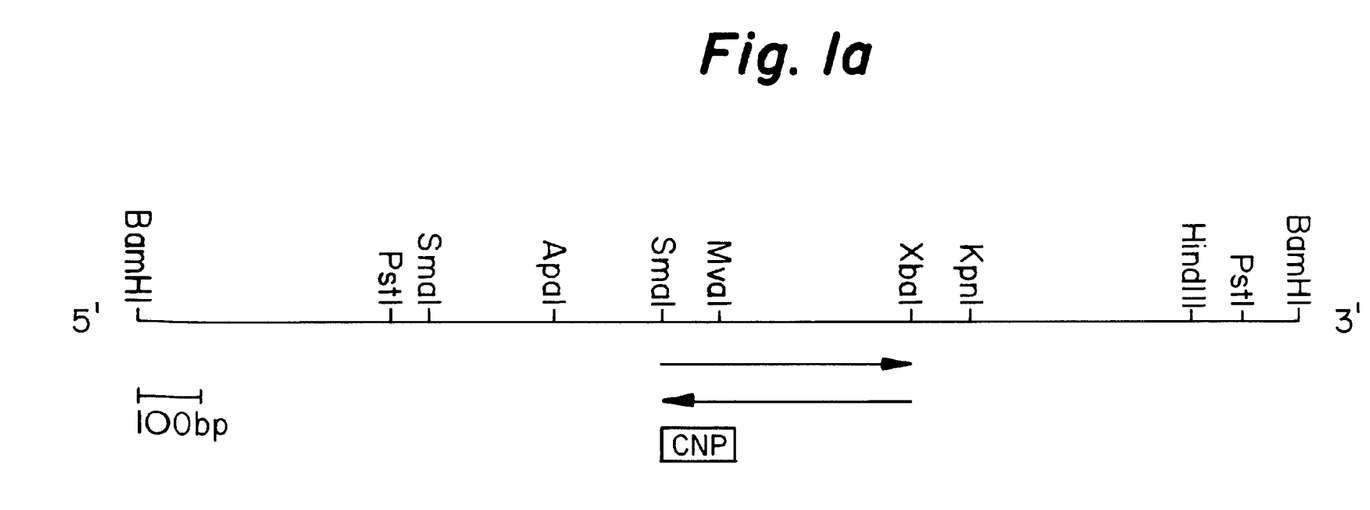
FIG. 1a shows the restriction enzyme map for the chromosomal gene of rCNP precursor protein (BamHI DNA fragment) and the region whose base sequence was determined.
Figure 1B:
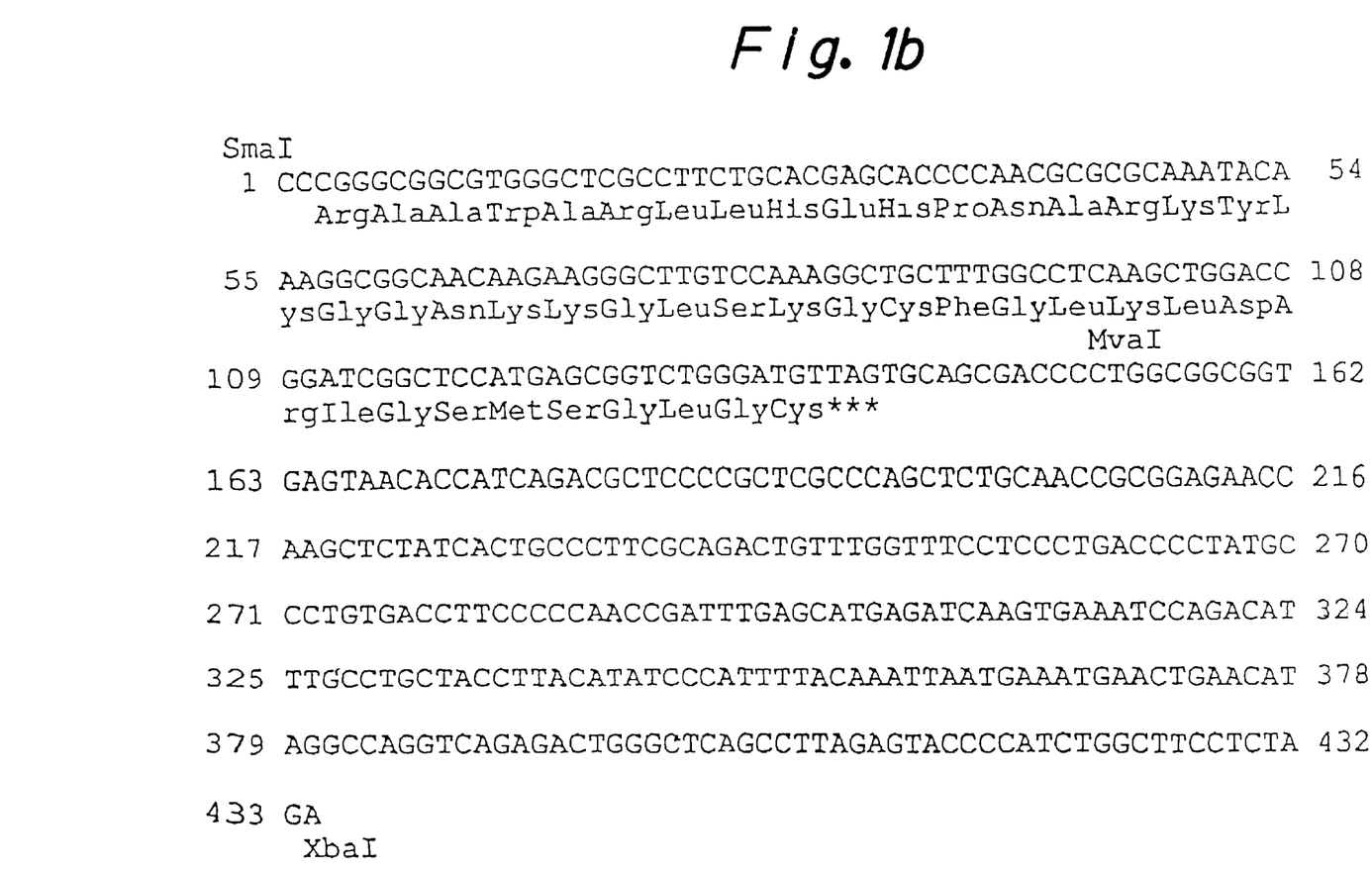
FIG. 1b shows the determined base sequence and the primary amino acid sequence of rCNP precursor protein encoded by it (see SEQ ID NO:4 and SEQ ID NO:5)

The restriction enzyme map for the BamHI fragment and the region whose base sequence was determined (as indicated by arrows) are shown in FIG. 1a, and the determined base sequence and the amino acid sequence encoded by it are shown in FIG. 1b.

In the next step, a library of rat brain cDNA was screened using as a probe a 150-bp DNA fragment coding for rCNP-22 that was sliced from the above-mentioned BamHI DNA fragment with restriction enzymes SmaI and MvaI (the 150-bp DNA fragment is hereunder referred to as rDC-22).

As a result, 22 clones were obtained that would hybridize with rDC-22 and of those 22 clones, the one carrying the longest (ca. 1 kbp) cDNA was found to be λrCNP 21. On the basis of this result, the whole base sequence of the cDNA fragment composed of ca. 1 kbp that was carried by said λrCNP 21 was determined. As a result, it was found that the cDNA fragment coded for the whole amino acid sequence of rCNP precursor protein (see FIG. 2).

First, the DNA fragment under discussion contained a long open reading frame starting with ATG that existed in positions 1–3 of the base sequence. Since this ATG was the first methionine codon that appeared in the cDNA and since the base sequence around that codon was in agreement with the consensus sequence of a translation initiation codon, A/G NNATG (N denotes either one of A, T, G and C), which is known to exist in eukaryotes, the present inventors estimated that the ATG of interest would be a translation initiation codon for the rCNP precursor. The open reading frame of interest was found to encode a polypeptide composed of 126 amino acid residues. It was also found that its primary amino acid sequence was in very good agreement with that of the pCNP precursor. On the basis of these findings, the present inventors were convinced that the cDNA obtained was definitely a cDNA coding for rCNP.

Figure 2A:
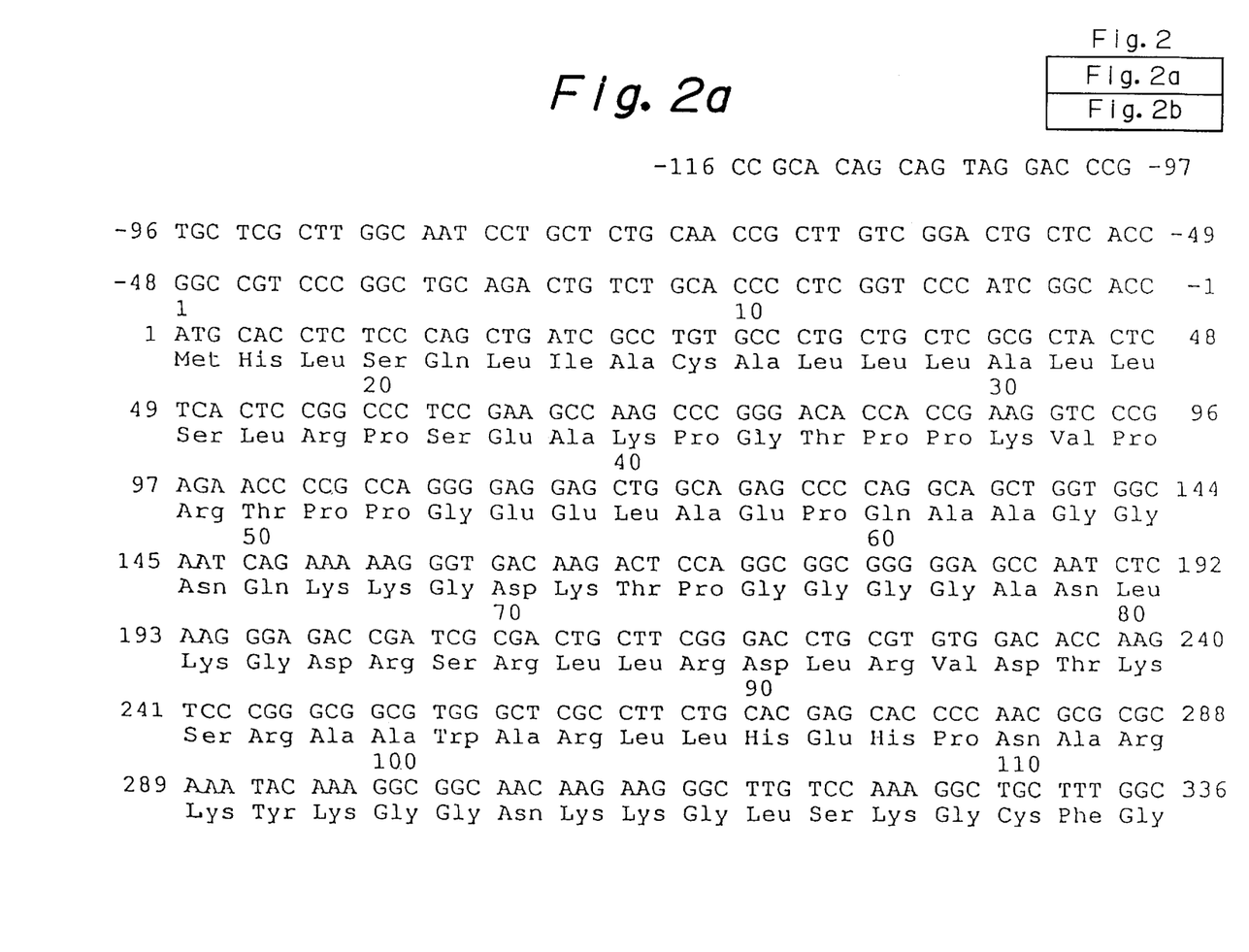
FIG. 2 shows the whole base sequence of CNP cDNA and the primary amino acid sequence of rCNP precursor protein encoded by it (see SEQ ID NO:6 and SEQ ID NO:7).
Figure 2B:
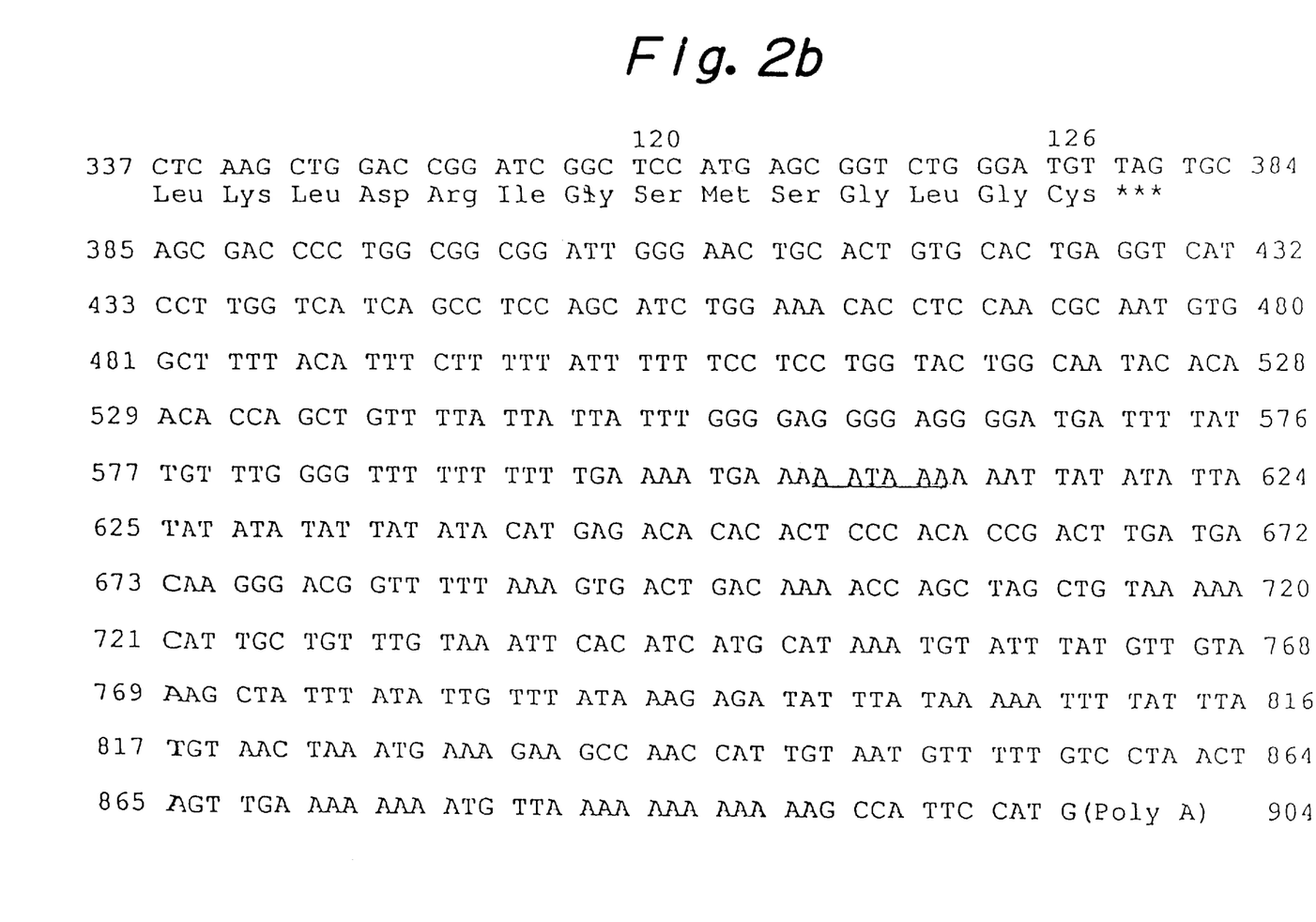

As described above, the present inventors isolated rCNP cDNA and analyzed it, thereby successfully identifying the rCNP precursor protein as a polypeptide composed of 126 amino acid residues having the primary amino acid sequence shown in FIG. 2. In the C-terminal region of the thus identified primary amino acid sequence of the rCNP precursor protein (which is hereunder abbreviated as prepro rCNP), rat CNP-22 that was the sequence corresponding to pCNP-22 whose structure was first determined from porcine brain (rCNP-22: positions 105–126 of the amino acid sequence shown in FIG. 2) and rat CNP-53 that was the sequence corresponding to pCNP-53 whose structure was also first determined from porcine brain (rCNP-53: positions 74–126 of the amino acid sequence shown in FIG. 2) and, in addition, pCNP-22 and pCNP-53 were in complete agreement with rCNP-22 and rCNP-53, respectively, in terms of amino acid sequence. For synthesis of those peptides, it would be indispensable that their precursor be cleaved with processing enzymes. Since the amino acid sequences of prepro rCNP in areas near positions 22 and 53 from the C-terminus of prepro rCNP where the processing would take place were in complete agreement between rat and porcine, the possibility that rCNP-22 or rCNP-53 is synthesized in rat's brain would be extremely high. Further, as in the case of porcine, a region rich in hydrophobic amino acid residues (in positions 10–16 of the primary amino acid sequence shown in FIG. 2) was present in the N-terminal region of prepro rCNP; hence, in view of this fact, there is a high possibility that the signal peptide necessary for secretion will exist in the N-terminal region of prepro rCNP.

With the above-discussed facts taken into consideration, rCNP-22 and rCNP-53 are presumably biosynthesized by the following pathway. First, prepro rCNP composed of 126 amino acid residues is translated from mRNA. Then, the signal peptide present in the N-terminal region of the prepro CNP is cleaved for conversion to pro rCNP in the process of secretion. Further, the pro rCNP is cleaved by processing enzymes at specific positions (between positions 73 and 74 of the primary amino acid sequence that is shown in FIG. 2 and between positions 104 and 105 of the same sequence) to be converted to rCNP-53 and rCNP-22.

In summary, the present inventors isolated cDNA coding for the precursor protein of rCNPs (rCNP-22 and rCNP-53) and analyzed them to identify the primary amino acid sequence of the rCNP precursor protein. At the same time, they successfully identified the structures of rat CNPs (rCNP-53 and rCNP-22) corresponding to porcine CNPs (pCNP-53 and pCNP-22). The present invention has been accomplished under these circumstances.

The following examples are provided for the purpose of further illustrating the present invention but are in no way to be taken as limiting.

EXAMPLE 1

Isolation of Chromosomal Gene Coding for Rat CNP Precursor Protein

*E. coli* strain K12 derived LE 392 was infected with a porcine chromosomal gene phage DNA library (product of Clonetech Co.) stored at 4° C. The cells were plated on an LB medium (10 g, bactotryptone; 5 g, yeast extract; 5 g, NaCl; 1.5%, bactoagar; total volume, 1 l) and cultivated overnight at 37° C. The plate was cooled at 4° C. for 30 min and a nitrocellulose filter (product of Shleicher & Schnell Co.) was left to stand on the phage plaque for 5 minutes. Subsequently, the filter was stripped from the plate, dried with air, immersed in an alkaline denaturation solution (0.5 M NaOH and 1.5 M NaCl) for 1 minute, and then immersed in a neutralizing solution (0.5 M Tris-HCl; pH 7.0; 1.5 M NaCl) for 1 minute. Thereafter, the nitrocellulose filter was rinsed with a 3×SSC solution (20×SSC NaCl, 175.3 g; trisodium citrate, 88.2 g; total volume, 1 l), dried with air and heat-treated under vacuum at 80° C. for 120 min.

Using the thus prepared nitrocellulose filter, plaque hybridization was performed under the following conditions. First, a prehybridization solution [3×SSC; 5×Denhardt's solution (consisting of albumin, polyvinyl pyrrolidone and Ficoll, each weighing 1 mg/ml); salmon sperm DNA, 100 μg/ml; 30% formamide; 0.1% SDS] was added to the nitrocellulose filter and prehybridization was conducted at 37° C. for 2 hours. Then, using $10^6$ cpm of the pDC-53 DNA probe (the method of its preparation is described by the present inventors in commonly assigned Japanese Patent Application No. 186583/1990) and 1 ml of the prehybridization solution for two sheets of the nitrocellulose filter, hybridization was performed overnight at 37°

C. Subsequently, the filter was washed three times with a 3×SSC solution containing 0.1% SDS, two washings done at 40° C. for 40 minutes and one washing at 55° C. for 30 minutes; the washed filter was dried with air and subjected to autoradiography at −80° C. for 24 h. By screening ca. $5\times10^5$ clones in this way, eight clones hybridizing with the pDC-53 DNA probe were obtained. One of those clones was named "λrCNP G3" and subjected to analyses in the subsequent stages.

EXAMPLE 2

Analysis of λrCNP G3 Phage and Determination of its base sequence

A. analysis of λrCNP G3 phage DNA

DNA was prepared from λrCNP G3 phage in the usual manner. Subsequently, the phage DNA was cleaved with restriction enzymes BamHI, EcoRI and PstI and the resulting DNA fragments were separated and analyzed by electrophoresis on an agarose gel. The λrCNP G3 was found to be a phage containing a ca. 14-kbp rat chromosomal gene. Analysis by Southern blotting using the pDC-53 DNA probe showed that each of BamHI DNA fragment of ca. 2.1 kbp, EcoRI DNA fragment of ca. 19 kbp and PstI DNA fragment of ca. 1.65 kbp hybridized with the pDC-53 DNA probe. The base sequence of part of the BamHI DNA (2.1 kbp) which hybridized with the pDC-53 DNA probe was determined by the following method.

B. Determining the base sequence of BamHI DNA fragment

In order to determine the base sequence of the BamHI DNA fragment, the latter was first subcloned in a plasmid vector pUC 118 (Takara Shuzo Co., Ltd.) at the BamHI site. From the resulting plasmid (pUC rCNP G3), a SmaI-XbaI DNA fragment (450 bp) hybridizing with the pDC-53 DNA probe was isolated and subcloned to phage vectors M13 mp18 and 19. Using a universal primer, with the resulting single-stranded DNA fragment being used as a template, the DNA base sequence of the BamHI DNA fragment of interest was determined by the dideoxy method with SEQUENASE (United States Biochemical Corporation) and a sequencer kit of Takara Shuzo Co., Ltd.

The base sequence of the BamHI DNA fragment of interest which was determined by the above-described method and the amino acid sequence as predictable from that base sequence are shown in FIG. 1b.

EXAMPLE 3

Preparation of DNA Probe (rDC-22)

The DNA probe (rDC-22) to be used for cloning cDNA coding for the rCNP precursor protein was prepared by the method consisting of cleaving the aforementioned plasmid pUC rCNP G3 with restriction enzymes SmaI and MvaI to isolate a 14-bp DNA fragment and then marking the DNA with [α-$^{32}$P] dCTP using a multi-prime labelling kit of Takara Shuzo Co., Ltd.

EXAMPLE 4

Isolation of Rat CNP cDNA

A. Preparation of λgt10 cNDA library

Using a guanidine-thiocyanate method, 1295 μg of total RNA was extracted and isolated from 2.7 g of rat's brain. Then, using an oligo(dT)-cellulose column, ca. 84 μg of poly(A)$^+$ RNA was prepared from 1295 μg of the total RNA. Subsequently, using 4 μg of poly (A)$^+$ RNA, a double-stranded cDNA was prepared by the method of Gubler and Hoffman (Gubler, U. et al., Gene, 25, 263, 1983). A 13-bp EcoRI adapter was ligated to the resulting cDNA and the product was subjected to size fractionation by 1% agarose gel electrophoresis. The thus obtained cDNA composed of 300–1500 bp was ligated to a phage λgt10 arm and by subsequent in vitro packaging, a cDNA library was prepared that consisted of 4.7–11.1×10$^6$ independent clones per microgram of poly(A)$^+$ RNA.

B. Screening the cDNA library

About 6×10$^5$ clones of the cDNA library obtained in step A were screened using the rDC-22DNA probe prepared in Example 4. The screening method was the the same as adopted in Example 2, except that c600hfl was used as cells and that the concentration of formamide in the hybridization solution was 50%, with 5×SSPE (20×SSPE, 3 M NaCl, 0.2 M sodium primary phosphate and 0.02 M EDTA). Two washings were conducted with 2×SSC containing 0.1% SDS at 65° C. for 40 min each time.

As a result of the screening, a clone was obtained that hybridized with the rDC-22 DNA probe and it was designated λrCNP 21.

C. Analysis of λcCNP phage and determination of its base sequence

First, DNA was prepared from the λrCNP 21 phage in the usual manner. Cleavage of this DNA with a restriction enzyme EcoRI showed that λrCNP 21 contained ca. 1 kbp of cDNA. For final analysis of the cDNA, the 1-kbp DNA fragment was first subcloned to M 13 phage and then the base sequence of the DNA was determined by a dideoxy method. The thus determined base sequence of the cDNA and the primary amino acid sequence as predictable from it are shown in FIG. 2.

As described on the foregoing pages, the present inventors isolated part of the rCNP gene from a rat chromosomal gene library using pDC-53 as a probe. With the isolated rCNP gene being used as a probe, a cDNA coding for the whole region of the rCNP precursor was successfully synthesized and isolated from mRNA derived from the rat brain. As a result, it was verified that a gene coding for CNP also existed in rats as well as in pigs. The present inventors further determined the whole structure of the rCNP precursor protein. As in pigs, the rCNP precursor protein in rats was composed of 126 amino acid residues and contained at the C-terminus the amino acid sequence that corresponded to pCNP-53 and pCNP-22 isolated from porcine brain. Since the amino acid sequences of those peptides at the processing site were in complete agreement between porcine and rat, it is predicted that those peptides would also be biosynthesized in rats through a pathway similar to that involved in pigs and that they would work as hormones or nerve transmitters that regulate the homeostatic balance of body fluid volume and blood pressure in vivo.

If the cDNA coding for the rCNP precursor is expressed in animal cells and if the protein or peptide secreted out of the cells is isolated and identified, the physiological activities of three novel peptides that are biosynthesized from the rCNP precursor but which cannot be synthesized from the pCNP precursor (i.e., modified species of prepro rCNP that are specifically cleaved at the C-terminus of lysine residues at positions 24 and 30 of the primary amino acid sequence and arginine residue at position 33) can be investigated.

What is worth particular note in the present invention is that the structures of rCNP-53 and rCNP-22 were identified as being entirely the same as those in pigs. This attests to the fact that the physiological activities of pCNP which have so far been evaluated with rats reflect on the correct measurement not influenced by differences in animal species.

Further, the sites of expression of CNPs in rats can be examined correctly by using the cDNA coding for the rat CNPs obtained in the present invention.

The information obtained by the present invention concerning the cDNA of the rCNP precursor protein and its primary amino acid sequence will make great contributions not only to future studies for unravelling the mechanism behind the biosynthesis and physiological actions of CNPs in mammals but also to the efforts to establish pharmaceutical applications of peptides assignable to the CNP family.

What is claimed is:

1. A isolated polypeptide having the following amino acid sequence (see SEQ ID NO:1):

Met His Leu Ser Gln Leu Ile Ala Cys Ala Leu Leu Leu Ala Leu Leu Ser Leu Arg Pro Ser Glu Ala Lys Pro Gly Thr Pro Pro Lys Val Pro Arg Thr Pro Pro Gly Glu Glu Leu Ala Glu Pro Gln Ala Ala Gly Gly Asn Gln Lys Lys Gly Asp Lys Thr Pro Gly Gly Gly Gly Ala Asn Leu Lys Gly Asp Arg Ser Arg Leu Leu Arg Asp Leu Arg Val Asp Thr Lys Ser Arg Ala Ala Trp Ala Arg Leu Leu His Glu His Pro Asn Ala Arg Lys Tyr Lys Gly Gly Asn Lys Lys Gly Leu Ser Lys Gly Cys Phe Gly Leu Lys Leu Asp Arg Ile Gly Ser Met Ser Gly Leu Gly Cys.

2. A DNA coding for a isolated polypeptide having the following amino acid sequence (see SEQ ID NO:1):

Met His Leu Ser Gln Leu Ile Ala Cys Ala Leu Leu Leu Ala Leu Leu Ser Leu Arg Pro Ser Glu Ala Lys Pro Gly Thr Pro Pro Lys Val Pro Arg Thr Pro Pro Gly Glu Glu Leu Ala Glu Pro Gln Ala Ala Gly Gly Asn Gln Lys Lys Gly Asp Lys Thr Pro Gly Gly Gly Gly Ala Asn Leu Lys Gly Asp Arg Ser Arg Leu Leu Arg Asp Leu Arg Val Asp Thr Lys Ser Arg Ala Ala Trp Ala Arg Leu Leu His Glu His Pro Asn Ala Arg Lys Tyr Lys Gly Gly Asn Lys Lys Gly Leu Ser Lys Gly Cys Phe Gly Leu Lys Leu Asp Arg Ile Gly Ser Met Ser Gly Leu Gly Cys.

3. An isolated DNA according to claim 2 which comprises the following base sequence (see SEQ ID NO:2):

ATG CAC CTC TCC CAG CTG ATC GCC TGT GCC CTG CTG CTC GCG CTA CTC TCA CTC CGG CCC TCC GAA GCC AAG CCC GGG ACA CCA CCG AAG GTC CCG AGA ACC CCG CCA GGG GAG GAG CTG GCA GAG CCC CAG GCA GCT GGT GGC AAT CAG AAA AAG GGT GAC MG ACT CCA GGC GGC GGG GGA GCC AAT CTC MG GGA GAC CGA TCG CGA CTG CTT CGG GAC CTG CGT GTG GAC ACC AAG TCC CGG GCG GCG TGG GCT CGC CTT CTG CAC GAG CAC CCC AAC GCG CGC AAA TAC AAA GGC GGC AAC MG AAG GGC TTG TCC AAA GGC TGC TTT GGC CTC MG CTG GAC CGG ATC GGC TCC ATG AGC GGT CTG GGA TGT.

4. An isolated DNA having the following base sequence (see SEQ ID NO:3):

CC GCA CAG CAG TAG GAC CCG TGC TCG CTT GGC AAT CCT GCT CTG CAA CCG CTT GTC GGA CTG CTC ACC GGC CGT CCC GGC TGC AGA CTG TCT GCA CCC CTC GGT CCC ATC GGC ACC ATG CAC CTC TCC CAG CTG ATC GCC TGT GCC GTG CTG CTC GCG CTA CTC TCA CTC CGG CCC TCC GAA GCC AAG CCC GGG ACA CCA CCG AAG GTC CCG AGA ACC CCG CCA GGG GAG GAG CTG GCA GAG CCC CAG GCA GCT GGT GGC AAT CAG AAA AAG GGT GAC AAG ACT CCA GGC GGC GGG GGA GCC AAT CTC AAG GGA GAC CGA TCG CGA CTG CTT CGG GAC CTG CGT GTG GAC ACC AAG TCC CGG GCG GCG TGG GCT CGC CTT CTG CAC GAG CAC CCC AAC GCG CGC AAA TAC AAA GGC GGC AAC AAG AAG GGC TTG TCC AAA GGC TGC TTT GGC CTC AAG CTG GAC CGG ATC GGC TCC ATG AGC GGT CTG GGA TCT TAG TGC AGC GAC CCC TGG CGG CGG ATT GGG AAC TGC ACT GTG CAC TGA GGT CAT CCT TGG TCA TCA GCC TCC AGC ATC TGG AAA CAC CTC CAA CGC AAT GTG GCT TTT ACA TTT CTT TTT ATT TTT TCC TCC TGG TAC TGG CAA TAC ACA ACA CCA GCT GTT TTA TTA TTA TTT GGG GAG GGG AGG GGA TGA TTT TAT TGT TTG GGG TTT TTT TTT TGA AAA TGA AAA ATA AAA AAT TAT ATA TTA TAT ATA TAT TAT ATA CAT GAG ACA CAC ACT CCC ACA CCG ACT TGA TGA CAA GGG ACG GTT TTT AAA GTG ACT GAC AAA ACC AGC TAG CTG TAA AAA CAT TGC TGT TTG TAA ATT CAC ATC ATG CAT AAA TGT ATT TAT GTT GTA AAG CTA TTT ATA TTG TTT ATA AAG AGA TAT TTA TAA AAA TTT TAT TTA TGT AAC TAA ATG AAA GAA GCC AAC CAT TGT AAT GTT TTT GTC CTA ACT AGT TGA AAA AAA ATG TTA AAA AAA AAA AAG CCA TTC CAT G(Poly A).

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 126 amino acids
      (B) TYPE: amino acid
      (C) STRANDEDNESS: single
      (D) TOPOLOGY: linear    (ii) MOLECULE TYPE: peptide    (xi) SEQUENCE DESCRIPTION: SEQ ID NO:1:

```
Met His Leu Ser Gln Leu Ile Ala Cys Ala Leu Leu Leu Ala Leu
1               5                   10                  15

Leu Ser Leu Arg Pro Ser Glu Ala Lys Pro Gly Thr Pro Pro Lys
                20                  25                  30

Val Pro Arg Thr Pro Pro Gly Glu Glu Leu Ala Glu Pro Gln Ala
                35                  40                  45

Ala Gly Gly Asn Gln Lys Lys Gly Asp Lys Thr Pro Gly Gly Gly
                50                  55                  60

Gly Ala Asn Leu Lys Gly Asp Arg Ser Arg Leu Leu Arg Asp Leu
                65                  70                  75

Arg Val Asp Thr Lys Ser Arg Ala Ala Trp Ala Arg Leu Leu His
                80                  85                  90

Glu His Pro Asn Ala Arg Lys Tyr Lys Gly Gly Asn Lys Lys Gly
                95                  100                 105

Leu Ser Lys Gly Cys Phe Gly Leu Lys Leu Asp Arg Ile Gly Ser
                110                 115                 120

Met Ser Gly Leu Gly Cys
                125
```

(2) INFORMATION FOR SEQ ID NO:2:

(i) SEQUENCE CHARACTERISTICS:
      (A) LENGTH: 378 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:2:

```
ATGCACCTCT CCCAGCTGAT CGCCTGTGCC CTGCTGCTCG CGCTACTCTC ACTCCGGCCC      60

TCCGAAGCCA AGCCCGGGAC ACCACCGAAG GTCCCGAGAA CCCCGCCAGG GGAGGAGCTG     120

GCAGAGCCCC AGGCAGCTGG TGGCAATCAG AAAAAGGGTG ACAAGACTCC AGGCGGCGGG     180

GGAGCCAATC TCAAGGGAGA CCGATCGCGA CTGCTTCGGG ACCTGCGTGT GGACACCAAG     240

TCCCGGGCGG CGTGGGCTCG CCTTCTGCAC GAGCACCCCA ACGCGCGCAA ATACAAAGGC     300

GGCAACAAGA AGGGCTTGTC CAAAGGCTGC TTTGGCCTCA AGCTGGACCG GATCGGCTCC     360

ATGAGCGGTC TGGGATGT                                                  378
```

(2) INFORMATION FOR SEQ ID NO:3:

(i) SEQUENCE CHARACTERISTICS:
        (A) LENGTH: 1020 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:3:

```
CCGCACAGCA GTAGGACCCG TGCTCGCTTG GCAATCCTGC TCTGCAACCG CTTGTCGGAC    60

TGCTCACCGG CCGTCCCGGC TGCAGACTGT CTGCACCCCT CGGTCCCATC GGCACCATGC   120

ACCTCTCCCA GCTGATCGCC TGTGCCCTGC TGCTCGCGCT ACTCTCACTC CGGCCCTCCG   180

AAGCCAAGCC CGGGACACCA CCGAAGGTCC CGAGAACCCC GCCAGGGGAG GAGCTGGCAG   240

AGCCCCAGGC AGCTGGTGGC AATCAGAAAA AGGGTGACAA GACTCCAGGC GGCGGGGGAG   300

CCAATCTCAA GGGAGACCGA TCGCGACTGC TTCGGGACCT GCGTGTGGAC ACCAAGTCCC   360

GGGCGGCGTG GCTCGCCTT  CTGCACGAGC ACCCCAACGC GCGCAAATAC AAAGGCGGCA   420

ACAAGAAGGG CTTGTCCAAA GGCTGCTTTG GCCTCAAGCT GGACCGGATC GGCTCCATGA   480

GCGGTCTGGG ATGTTAGTGC AGCGACCCCT GGCGGCGGAT TGGGAACTGC ACTGTGCACT   540

GAGGTCATCC TTGGTCATCA GCCTCCAGCA TCTGGAAACA CCTCCAACGC AATGTGGCTT   600

TTACATTTCT TTTTATTTTT TCCTCCTGGT ACTGGCAATA CACAACACCA GCTGTTTTAT   660

TATTATTTGG GGAGGGGAGG GGATGATTTT ATTGTTTGGG GTTTTTTTTT TGAAAATGAA   720

AAATAAAAAA TTATATATTA TATATATATT ATATACATGA GACACACACT CCCACACCGA   780

CTTGATGACA AGGGACGGTT TTTAAAGTGA CTGACAAAAC CAGCTAGCTG TAAAAACATT   840

GCTGTTTGTA AATTCACATC ATGCATAAAT GTATTTATGT TGTAAAGCTA TTTATATTGT   900

TTATAAAGAG ATATTTATAA AAATTTTATT TATGTAACTA AATGAAAGAA GCCAACCATT   960

GTAATGTTTT TGTCCTAACT AGTTGAAAAA AAATGTTAAA AAAAAAAAAG CCATTCCATG  1020
```

(2) INFORMATION FOR SEQ ID NO:4:

(i) SEQUENCE CHARACTERISTICS:
        (A) LENGTH: 45 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:4:

```
Arg Ala Ala Trp Ala Arg Leu Leu His Glu His Pro Asn Ala Arg
1               5                  10                  15

Lys Tyr Lys Gly Gly Asn Lys Lys Gly Leu Ser Lys Gly Cys Phe
                20                  25                  30

Gly Leu Lys Leu Asp Arg Ile Gly Ser Met Ser Gly Leu Gly Cys
                35                  40                  45
```

(2) INFORMATION FOR SEQ ID NO:5:

(i) SEQUENCE CHARACTERISTICS:
        (A) LENGTH: 434 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:5:

```
CCCGGGCGGC GTGGGCTCGC CTTCTGCACG AGCACCCCAA CGCGCGCAAA TACAAAGGCG      60

GCAACAAGAA GGGCTTGTCC AAAGGCTGCT TTGGCCTCAA GCTGGACCGG ATCGGCTCCA     120

TGAGCGGTCT GGGATGTTAG TGCAGCGACC CCTGGCGGCG GTGAGTAACA CCATCAGACG     180

CTCCCCGCTC GCCCAGCTCT GCAACCGCGG AGAACCAAGC TCTATCACTG CCCTTCGCAG     240

ACTGTTTGGT TTCCTCCCTG ACCCCTATGC CCTGTGACCT TCCCCCAACC GATTTGAGCA     300

TGAGATCAAG TGAAATCCAG ACATTTGCCT GCTACCTTAC ATATCCCATT TTACAAATTA     360

ATGAAATGAA CTGAACATAG GCCAGGTCAG AGACTGGGCT CAGCCTTAGA GTACCCCATC     420

TGGCTTCCTC TAGA                                                       434
```

(2) INFORMATION FOR SEQ ID NO:6:

(i) SEQUENCE CHARACTERISTICS:
        (A) LENGTH: 126 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:6:

```
Met His Leu Ser Gln Leu Ile Ala Cys Ala Leu Leu Leu Ala Leu
1               5                   10                  15

Leu Ser Leu Arg Pro Ser Glu Ala Lys Pro Gly Thr Pro Pro Lys
            20                  25                  30

Val Pro Arg Thr Pro Pro Gly Glu Glu Leu Ala Glu Pro Gln Ala
            35                  40                  45

Ala Gly Gly Asn Gln Lys Lys Gly Asp Lys Thr Pro Gly Gly Gly
            50                  55                  60

Gly Ala Asn Leu Lys Gly Asp Arg Ser Arg Leu Leu Arg Asp Leu
            65                  70                  75

Arg Val Asp Thr Lys Ser Arg Ala Ala Trp Ala Arg Leu Leu His
            80                  85                  90

Glu His Pro Asn Ala Arg Lys Tyr Lys Gly Gly Asn Lys Lys Gly
            95                  100                 105

Leu Ser Lys Gly Cys Phe Gly Leu Lys Leu Asp Arg Ile Gly Ser
            110                 115                 120

Met Ser Gly Leu Gly Cys
            125
```

(2) INFORMATION FOR SEQ ID NO:7:

(i) SEQUENCE CHARACTERISTICS:
        (A) LENGTH: 1020 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:7:

```
CCGCACAGCA GTAGGACCCG TGCTCGCTTG GCAATCCTGC TCTGCAACCG CTTGTCGGAC      60

TGCTCACCGG CCGTCCCGGC TGCAGACTGT CTGCACCCCT CGGTCCCATC GGCACCATGC     120

ACCTCTCCCA GCTGATCGCC TGTGCCCTGC TGCTCGCGCT ACTCTCACTC CGGCCCTCCG     180

AAGCCAAGCC CGGACACCA CCGAAGGTCC CGAGAACCCC GCCAGGGGAG GAGCTGGCAG      240

AGCCCCAGGC AGCTGGTGGC AATCAGAAAA AGGGTGACAA GACTCCAGGC GGCGGGGAG      300
```

-continued

```
CCAATCTCAA GGGAGACCGA TCGCGACTGC TTCGGGACCT GCGTGTGGAC ACCAAGTCCC    360

GGGCGGCGTG GGCTCGCCTT CTGCACGAGC ACCCCAACGC GCGCAAATAC AAAGGCGGCA    420

ACAAGAAGGG CTTGTCCAAA GGCTGCTTTG GCCTCAAGCT GGACCGGATC GGCTCCATGA    480

GCGGTCTGGG ATGTTAGTGC AGCGACCCCT GGCGGCGGAT TGGGAACTGC ACTGTGCACT    540

GAGGTCATCC TTGGTCATCA GCCTCCAGCA TCTGGAAACA CCTCCAACGC AATGTGGCTT    600

TTACATTTCT TTTTATTTTT TCCTCCTGGT ACTGGCAATA CACAACACCA GCTGTTTTAT    660

TATTATTTGG GGAGGGGAGG GGATGATTTT ATTGTTTGGG GTTTTTTTTT TGAAAATGAA    720

AAATAAAAAA TTATATATTA TATATATATT ATATACATGA GACACACACT CCCACACCGA    780

CTTGATGACA AGGGACGGTT TTTAAAGTGA CTGACAAAAC CAGCTAGCTG TAAAAACATT    840

GCTGTTTGTA AATTCACATC ATGCATAAAT GTATTTATGT TGTAAAGCTA TTTATATTGT    900

TTATAAAGAG ATATTTATAA AAATTTTATT TATGTAACTA AATGAAAGAA GCCAACCATT    960

GTAATGTTTT TGTCCTAACT AGTTGAAAAA AAATGTTAAA AAAAAAAAAG CCATTCCATG   1020
```